United States Patent
Schrooyen et al.

(10) Patent No.: US 7,169,896 B2
(45) Date of Patent: Jan. 30, 2007

(54) KERATIN-BASED PRODUCTS AND METHODS FOR THEIR PRODUCTIONS

(75) Inventors: Peter Marcel Myriam Schrooyen, Barendrecht (NL); Radulf Oberthur, Bawinkel (DE)

(73) Assignee: Stichting Nederlands Instituut voor Zuivelonderzoek, Ede (NL)

( * ) Notice: Subject to any disclaimer, the term of this patent is extended or adjusted under 35 U.S.C. 154(b) by 44 days.

(21) Appl. No.: 10/483,566

(22) PCT Filed: Jul. 12, 2002

(86) PCT No.: PCT/NL02/00469

§ 371 (c)(1),
(2), (4) Date: Jun. 6, 2004

(87) PCT Pub. No.: WO03/006531

PCT Pub. Date: Jan. 23, 2003

(65) Prior Publication Data

US 2004/0210039 A1 Oct. 21, 2004

(30) Foreign Application Priority Data

Jul. 13, 2001 (EP) .................................. 01202694

(51) Int. Cl.
*C07K 1/00* (2006.01)
(52) U.S. Cl. ........................................ 530/350; 512/14

(58) Field of Classification Search ................ 530/350; 512/14

See application file for complete search history.

(56) References Cited

U.S. PATENT DOCUMENTS 4,279,996 A 7/1981 Yoshioka et al.

OTHER PUBLICATIONS

P.M.M. Schrooyen, P.J. Dijkstra, R.C. Oberthur, A.Bantjes, J.Feijen: "Partially Carboxylated Feather Keratins. 2. Thermal and Mechanical Properties of Films" J, Agric. Food Chem., vol. 2001, No. 49, Dec. 16, 2000, pp. 221-230, XP002187325.
P.M.M. Schrooyen, P.J. Dijkstra, R.C. Oberthur, A.Bantjes, J.Feijen: "Partially Carboxymethylated Feather Keratins. 1. Properties in Aqueous Systems"J. Agric. Food Chem., vol. 2000, No. 48, Aug. 16, 2000, pp. 4326-4334, XP002187326 cited in the application.

*Primary Examiner*—Karen Cochrane Carlson
*Assistant Examiner*—Agnes Rooke
(74) *Attorney, Agent, or Firm*—Young & Thompson

(57) ABSTRACT

The present invention relates to a process for solubilizing keratins from a keratin containing starting material such as poultry feathers. The keratins are may be solubilized using a sulphide under alkaline conditions. In the process the cysteine residues of solubilized keratins and are partially modified, e.g. by alkylation. The conditions of solubilisation and partial modification are chosen such that the keratins are also partially hydrolyzed. The partially modified and partially hydrolyzed keratin may be used as stable dispersions e.g. for the production of films and coatings by casting.

20 Claims, 3 Drawing Sheets

KERATIN-BASED PRODUCTS AND METHODS FOR THEIR PRODUCTIONS

FIELD OF THE INVENTION

The present invention relates to new products derived from keratins. In particular, the invention relates to products that are derived from naturally occurring sources of keratin and keratin fibres, such as poultry feathers. The invention also relates to methods for the preparation of such keratin-derived products and to uses of such keratin-derived products.

BACKGROUND OF THE INVENTION

Feathers are an important waste product of the poultry industry, with about 4 million tons being produced per year world-wide. Although minor amounts thereof find use in for instance clothing, insulation and bedding, as well as a larger amount in the preparation of feather meal for the production of animal feed, there are currently insufficient (economically interesting) applications for such large quantities of feathers. As for environmental reasons, burning or burying of feathers is not always a practical alternative; these amounts of waste feathers present a difficult disposal problem for industries such as the poultry industry.

Thus, it is a general object of the invention to provide a range of economically viable uses of waste feathers, as well as to provide processes via which waste feathers can be put to such uses.

Feathers mainly consist of a fibrous protein material called keratin. Keratins are water-insoluble and protease-resistant proteins with a molecular weight of approximately 10 kDa. As shown in FIG. 1, each keratin molecule—indicated as (A) in FIG. 1—consists of a central part ($\beta$) which forms a crystalline $\beta$-sheet, and two randomly ordered chain ends, indicated as (N) and (C) respectively. In the feather, the central parts ($\beta$) of multiple keratins are joined to form a so-called microfibril (B) of about 30 angstroms in diameter. The chain ends (C) and (N) contain inter- and intra-chain cross-links (C) in the form of disulphide bonded dimeric amino acids (cystine) and form the amorphous matrix in which the microfibril is embedded. The disulphide bonds (C) and the molecular organisation of the proteins in the feathers impart insolubility and resistance to most proteolytic enzymes.

There is already an extensive amount of prior art relating to keratins, keratin-hydrolysates and products derived from keratins, as well as to the preparation and uses thereof. Especially the cosmetic and textile industries are interested in keratin-derived products for styling and modifying hair and wool. Shampoos and nail polish with hydrolysed keratin are just examples of prior art formulations that make use of keratins. Even though these applications are numerous, they are basically product formulations using mostly hydrolysed keratin as one of the components. Such products have a low added value and are of only limited use.

Prior art where keratins are used as a polymer in films or coatings is much less abundant as is evident from a review of this art in the thesis of one of the inventors (P. Schrooyen: "Feather keratins: modification and film formation", 1999, Thesis University of Twente, Enschede, The Netherlands). Generally, according to the processes described in these references, the insoluble keratins are extracted from their natural source and solubilised, e.g. in an aqueous medium. Usually, such extraction/solubilisation involves at least disruption of the disulphide bonds (C), which breaks up the microfibrils (B) to provide the separate(d) keratin molecules (A). Depending upon the conditions used, the extraction/solubilisation may also involve hydrolysis/degradation of the keratin molecules (A) themselves, i.e. cleavage of the peptide bonds between the amino acids that form the keratin molecule(s) (A). Disruption of disulphide bonds has reportedly been achieved by oxidation of the disulphide bonds with organic peracids to form sulphonic acid groups; by sulphitolysis of the disulphide bonds to form S-sulphonate groups; or by reduction of the disulphide bonds with thiol compounds such as 2-mercaptoethanol, dithiothreitol (DTT) or dithioerytritol, or by treatment with alkali metal sulphides such as a sodium sulphide solution. Generally, the purpose of the prior art processes is to provide a keratin-derived product that is soluble in aqueous media, e.g. a solution of keratin(s) or keratin hydrolysate. For this purpose, the art describes modification of the disrupted disulphide bonds so as to avoid reformation of the bonds and/or the use of specific additives to keep the keratins in solution or to otherwise stabilise the keratin solutions, such as alkali metal hydroxides, urea, guanidine hydrochloride, 2-mercaptoethanol or thioglycolate.

E.g. U.S. Pat. No. 3,464,825 describes a process in which keratins are extracted from feathers using an alkali metal sulphide solution, such as a $Na_2S$-solution. The keratin-solution thus obtained is then treated with an alkali metal sulphite such as a $Na_2SO_3$, after which the protein is acid-precipitated. The precipitated keratin is then solubilised in a aqueous alkali and subsequently oxidised using a water soluble oxidising agent, e.g. hydrogen peroxide, sodium periodate, sodium chlorite or an organic peracid such as peracetic acid or performic acid, which is believed to oxidise the cystine/cysteine residues to cysteic acid groups, However, the thus obtained keratins are essentially completely modified, i.e. all free cystine/cysteine residues are oxidised to cysteic acid groups. As a result the completely modified keratins are generally water-soluble and, therefore, less suited to provide water-insoluble films, e.g. for applications in coatings and for other applications mentioned hereinbelow. Also FR 2 522 657 describes essentially complete modification, e.g. of at least 70% of the free —SH groups of the keratins.

In contrast, U.S. Pat. No. 3,642,498, describes a process for the solubilisation of keratins using sodium sulphide whereby the cystine/cysteine groups remain essentially unmodified. The keratins are again extracted using an a metal sulphide solution, treated with an alkali metal sulphite solution, and then acid-precipitated. The resulting protein product is described as being dispersible in water-alcohol mixtures, and can be used for preparing films and coatings. U.S. Pat. No. 3,642,498 also describes alternative processes for extracting and solubilising feather keratins, including treatment with mercaptoethanol-alcohol-water mixtures; or treatment with alkaline mercaptoethanol-alcohol-water mixtures containing alkali metal hydroxides. However, according to U.S. Pat. No. 3,642,498, the cystine/cysteine groups remain essentially unmodified. A major disadvantage of solubilised keratins with essentially unmodified cystine/cysteine is that they do not allow to produce keratin-based products, in particular films and coatings, with the desired mechanical properties. In particular, such films suffer from brittleness.

Most of the art mentioned thus far dates back to the late 1960's and early 1970's. Nevertheless, in the 30 years since, these references have not led to any widespread use of the keratin-derived products disclosed therein. This is probably because the products and processes described are not economically viable—despite the fact that they employ waste feathers as a starting material—and/or because the keratin products obtained do not show the properties required for practical (e.g. commercial) use.

Some of these problems are addressed in the thesis of one of the inventors (P. Schrooyen; "Feather keratins: modification and film formation", 1999, Thesis University of Twente, Enschede, The Netherlands) that describes keratin-derived products obtained by partial modification (i.e., alkylation) of intact feather keratins using monoiodoacetamide, monoiodoacetic acid or monobromosuccinic acid in concentrated aqueous urea solution and in the presence of 2-mercaptoethanol. The keratins were modified to degrees of modification varying between 25 and 87%, calculated on the basis of the amount of remaining free —SH groups. This partial modification provided stable dispersions of essentially intact (i.e. non-hydrolysed), partially modified keratins, which could be used to cast strong films with desired thermal and mechanical properties. However, extraction and solubilisation of essentially intact keratins for partial modification requires the use of high concentrations of chemicals such as urea and 2-mercaptoethanol. The use of these chemicals at experimental scale is acceptable. However, their use at large scale is not economically feasible because the use of these chemicals is expensive, also in view of the environmental and occupational hazards associated with the use of these chemicals, requiring expensive precautionary measures.

Thus, there is still a need for an economically viable method for the processing of keratin-containing (waste) materials such as feathers, which method can be used to provide a range of keratin-based products, in particular films and coatings, with properties acceptable for practical/commercial application(s).

DESCRIPTION OF THE INVENTION

It has now been found that improved keratin-based products can be obtained by a process which involves a combination of partial degradation, usually by means of hydrolysis, of the keratin molecules and partial modification of the free —SH groups, i.e. the free —SH groups resulting from cleavage of the disulphide bonds (C). In particular, the invention provides such a partially degraded and partially modified product that is dispersible in water and that can be used in a range of applications, including but not limited to those discussed hereinbelow. Such water-dispersible, partially degraded and partially modified keratin-based products have not yet been described in the art.

Thus, in a first aspect, the invention relates to a process for producing partially modified and partially degraded keratin. The process comprises the steps of (a) solubilising keratin from a keratin-fibre containing starting material in an aqueous solution using a reducing agent at alkaline pH; and (b) partially modifying the —SH groups of the solubilised keratin. Preferably the conditions of steps (a) and/or (b) are such that the solubilised keratin is partially hydrolysed or partially degraded to a degree further specified hereinbelow. Optionally a further step (c) may be used to hydrolyse the keratin to a desired degree.

For the keratin-fibre containing starting material any suitable source of keratin fibres may be used. In particular, natural sources of keratin fibres may be used, such as e.g. hair, feathers, hoofs, nails, horns and the like. Preferably, a source of keratin fibres containing at least β-keratin is used. Feathers are an especially preferred starting material, in particular feathers of chicken, turkey, ducks, geese or other poultry, e.g. as obtained as a waste product from the poultry industry. These sources of keratin fibre may contain minor amounts of other proteins and/or other components such as fat or blood, e.g. usually amounts of less than 5% of total weight (based on dry feathers). Generally, the presence thereof may be tolerated, otherwise, some or all of these non-keratin components may be removed, prior to the solubilisation in step (a). The keratin-fibre containing stating material is preferably subjected to one or more pretreatments such as e.g. cleaning, washing, sorting, defatting, cutting, milling, grinding, drying, or any combination thereof. Such pretreatment may facilitate the handling of the starting material, it may improve the efficiency of further processing steps, such as solubilisation of the keratin, and/or it way improve the quality of the final keratin-based product. Alternatively, an already pre-processed keratin-containing starting material may be used, such as feather meal; as well as already isolated keratins or keratin fibres (which however for economic reasons will usually be less preferred). It is also encompassed in the scope of the invention to use a natural source of keratin or keratin fibres—e.g. feathers—directly in the solubilisation step a), without any further pre-treatment.

The reducing agent for solubilisation at alkaline pH may be chosen from sulphides, thiols, boric hydride and phosphines, or combinations thereof. Preferred sulphides are alkali metal sulphides, such as sodium sulphide. At lower alkaline pH, e.g. at a pH lower than 10, 9.5 or 9.0, ammonium sulphide may also be used as reducing agent for solubilisation, the use of which allows to avoid a salt residue in the final product. Preferred thiols are dithiothreitol, 2-mercaptoethanol and thioglycolate and a preferred phosphine is tri-n-butylphosphine.

The conditions of solubilisation, i.e. the concentrations of the keratin-fibre containing starting material, the reducing agent(s), and buffer, and the pH, temperature and duration of solubilisation are preferably chosen such that a satisfactory yield of solubilised keratins is obtained, preferably at least 10, 20, 30, 40, 50 or 60% of the keratin in the keratin-fibre containing starting material are solubilised. The conditions of solubilisation are further preferably chosen such that the solubilised keratin is partially hydrolysed or partially degraded to a degree further specified hereinbelow.

Preferably at least 10 g of keratin-fibre containing starting material is solubilised per liter of (aqueous) solubilisation medium, and preferably no more than 100 g of keratin-fibre containing starting material is solubilised per liter of (aqueous) solubilisation medium. Usually between 20 and 60 g of keratin-fibre containing starting material is solubilised per liter of (aqueous) solubilisation medium.

The concentration of the reducing agent in the (aqueous) solubilisation medium, e.g. an alkali metalsulphide or ammonium sulphide is preferably between 0.05 M and 1.0 M. Alternatively, using the combination of 2-mercaptoethanol and sodium hydroxide: 2-mercaptoethanol is used at a concentration between 0.1 M and 1.5 M in combination sodium hydroxide at between 0.1 and 1.0 N.

The pH at which the keratins are solubilised is alkaline, i.e. higher than pH 7.0 . Preferably however, solubilisation is performed at an alkaline pH that is et least pH 8.0, 8.5, 9.0, 9.5, however, more preferably the pH is at least or higher than pH 10.0, 10.5, 11.0, 11.5, 12.0, or 12.5 because at a pH at least or higher than pH 10.0 the dissociation equilibrium of sulphide shifts towards $S^{2-}$, which is a stronger reductor than is $HS^-$. Preferably the pH is not higher than pH 13.5.

The temperature at which the keratins are solubilised preferably is at least 20° C. However, preferably higher temperatures are used for solubilisation, such as a temperature of preferably at least 30, 40, 50, 60, 70 or 80° C., but preferably not higher than 100° C.

The duration of the keratin solubilisation step is primarily chosen such that the desired degree of hydrolysation of the solubilised keratin is obtained under the given solubilisation conditions. Typically the solubilisation will take between 10 minutes and 24 hours. The duration of the keratin solubilisation may be further optimised for the yield of solubilisation. Thus the skilled person will empirically optimise the set of conditions for keratin solubilisation in order to obtained at least the desired degree of keratin hydrolysis and preferably the highest yield of solubilised keratin.

In addition to the solubilisation of the keratin, the process of the invention further comprises the step of partially modifying the —SH groups present in the keratin. Generally, these —SH groups will be free —SH groups that result from the cleavage of the intra- and intermolecular disulphide bonds (C) in the keratin molecules, as may occur during the solubilisation under reducing conditions of the keratin from the keratin-fibre containing starting material. Thus, usually, the free —SH groups will be cysteine residues. The partial modification of the free —SH groups generally involves chemical conversion of the —SH group to another group, e.g. a functional group including but not limited to one or more of the functional groups mentioned hereinbelow. One purpose of the modification is that it excludes the modified —SH groups from (re)forming intra- and intermolecular disulphide bonds between the solubilised keratin molecules, thereby avoiding or at least reducing the formation of insoluble keratin aggregates. On the other hand partial modification of the —SH groups means that the remaining free cysteine residues are available for further reaction, e.g. (re)formation of disulphide linkages, for crosslinking and/or for polymerisation, which reactions may be used to impart desired properties upon the final product, such as mechanical strength and/or resistance against chemical or physical influences. Some further advantages of partial modification—compared to essentially complete modification—include that the keratins thus obtained are (better) suited to provide water-insoluble films, e.g. for applications in coatings and for other applications mentioned hereinbelow. By comparison, fully modified keratins, such as those described in U.S. Pat. No. 3,464,825 mentioned above, are generally water-soluble. The partial modification of the free —SH groups of the solubilised keratin may be achieved in a number of manners known per se, which will mainly depend upon the functional group(s) used. By manner of non-limiting example, some suitable functional groups as well as conditions for partially converting the free —SH groups will be mentioned hereinbelow.

In the process of the invention the partial modification of the solubilised keratin is preferably such that at least 10%, preferably at least 20%, more preferably at least 30% and most preferably at least 40% of all free —SH groups in the solubilised keratin is modified, and at the same time such that less than 70%, preferably no more than 65%, more preferably no more than 60% and most preferably no more than 57% of all free —SH groups in the solubilised keratin is modified. Ultimately preferred is a degree of modification of the all free —SH groups in the solubilised keratin is about 50%, i.e. between 44 and 56%. The remaining —SH groups in the keratin will not be modified and thus will still be present as such in the partially modified product obtained, or as re-formed disulphide bonds (which will be considered equivalent to two free —SH groups, e.g. for the purposes of calculating the degree of modification as described below).

The degree of modification may be controlled by suitably choosing the conditions of the modification reaction, including but not limited to the functionalising agent used, the reaction time, the temperature, the pH, the solvent(s) used, the concentrations of the respective reactants, and the concentration of the keratin material. It is envisaged that the selection of the specific conditions that will lead to a final product with the desired degree of modification may require some preliminary experiments and/or some degree of trial and error. However, based upon the disclosure herein, this will be within easy reach of the skilled person and should therefore be considered encompassed within the scope of the invention.

The modification is carried out in a manner known per se, depending upon the group or groups used to modify the —SH groups and whether this modification is combined with any further processing steps, e.g. the solubilisation. Suitable conditions may include the use of water or an aqueous medium at a concentration of the functionalising agent between 0.01M and 1M, at a pH of between 7.0 and 10.0, at a temperature of between 4° C. and 20° C., during a time of between 10 minutes and 24 hours, and at concentration of solubilised keratin of between 2 g and 10 g per 100 ml of the aqueous hydrolysis medium. Preferred conditions for modification with monochoroacetic acid at a degree of modification of about 50% are e.g. an incubation for 30–90 minutes of 10–30 g solubilised keratin in a volume of 1 liter with 0.5–5 g monochloroacetic acid, at a pH between 8.5 and 9.5, and at a temperature between 10–20° C.

The degree of modification may be determined by comparing the amount of free —SH groups remaining after modification (including the amount of disulphide bonds present) with the amount of free —SH groups (including disulphide bonds) prior to modification, in which amount of free —SH groups/disulphide bonds in a keratin preparation may be determined using a suitable assay, such as the DTNB/NTSB assay as described by Schrooyen et al. (Journal of Agricultural and Food Chemistry; 2000; 48(9); 4326–4334). Alternatively, the amount of free —SH groups and/disulphide bonds remaining after modification may also be compared to a theoretical value for the amount of —SH groups/disulphide bonds in keratin. The theoretical amount of —SH groups/disulphide bonds in native keratin (based upon the amount of cystine/cysteine residues present) is about 700 μmol cysteine groups/g keratin (with the amount of cystine groups being half that amount).

The —SH group may be modified with any desired functional group suited for the functionalisation of —SH groups and/or for the functionalisation of keratins; or with a suitable combination of two or more of such groups. The specific functional group(s) chosen and the respective amounts thereof, will usually depend upon the desired properties of the final product.

Thus, the keratins of the invention may be provided with one or more negatively charged functional groups; one or more positively charged functional groups; and/or one or more neutral functional groups; or a suitable combination thereof. In this respect, it will be clear to the skilled person that a "positively" and/or "negatively" charged group may be associated with a suitable counter-ion, i.e. an anion (i.e. group) or cation (i.e. group) respectively. It will also be clear that the actual charge carried by a "positively" or "negatively" charged functional group as described herein may also depend upon the conditions in which the keratins are present/maintained, such as the pH, the solvent, etc. Generally, however, at a pH in the range of 6.0 to 8.0 a "positively" charged group will have a net positive charge, a "negatively" charged group will have a net negative charge, and a "neutral" group will have a net charge of essentially zero.

Preferably, the functional groups described will be introduced using one or more saturated or unsaturated organic compounds that at least contain a group or residue that allows the organic compound to react with an —SH group. These may include but are not limited to suitable leaving groups such as halogen (chloro, bromo or iodo-); epoxide- or glycidyl-groups or unsaturated groups such as (meth)acryl, vinyl; and other suitable groups will be clear to the skilled person. Besides the group that may react with the free —SH groups, these organic compounds may be also contain one or more further groups that may provide for a negative charge, such as a —COOH group; or that may provide for a positive charge, such as an quaternary amine-group, including but not limited to alkylated amine groups. Thus, for instance, the keratin may be modified with negatively charged groups, e.g. those that can be introduced using for example:

halogenated acids such as chloroacetic acid; iodoacetic acid and bromoacetic acid.
peroxides such as hydrogen peroxide or organic peroxides, including but not limited to performic acid or peracetic acid to form sulphonate groups;
unsaturated organic compounds that contain negatively charged groups, such as vinyl compounds containing a —COOH group;
glycidyl compounds;

or any suitable combination thereof

Usually, partially modifying a partially hydrolysed keratin with such negatively charged groups will enhance the dispersibility of the keratins.

Positively charged functional groups may for example be introduced using:

halogenated organic amines, such as halogenated alkylamines;
glycidyl compounds carrying an amine group such as glycidyltrimethylammoniumchloride;

or a suitable combination thereof.

Neutral functional groups may for instance be introduced using:

halogenated organic compounds such as halogenated alkanes and halogenated ethers, esters or amides;
glycidyl compounds such as alkylglycidyl compounds;
vinylcompounds such as alkylvinylcompounds;

or a suitable combination thereof

Other suitable functionalising compounds are for instance described in FR 2 522 657. The keratins may also be modified using sulphites such as e.g. sodium sulphite or sodium metabisulphite to form S-sulfonate groups, or using other inorganic compounds.

It may be convenient to combine the modification step with the solubilisation step, e.g. by adding the functionalising agent to the solubilisation mixture. After solubilisation and modification the keratin-derived product may already be suitable for its intended final use, and thus for instance may be marketed or otherwise provided as such to the end-user.

In the process of the invention, the conditions of solubilisation and/or modification are preferably such that the solubilised keratin is partially hydrolysed or partially degraded. Partial hydrolysis—also referred to as partial "degradation"—generally comprises cleavage of (part of) the peptide bonds between the amino acids that form the keratin molecule. Partial hydrolysis may be achieved during solubilisation and/or modification. However, if solubilisation and/or modification does not produce the desired degree of partial hydrolysis of the solubilised keratin, further hydrolysis or degradation may be achieved by any manner known per se in the art, including e.g. chemical hydrolysis, physical hydrolysis and/or enzymatic hydrolysis.

The degree of hydrolysis of the solubilised keratin is such that a keratin-based product produced from the solubilised and partially hydrolysed keratin has the required physical and chemical properties. E.g. a film or coating produced from the solubilised and partially hydrolysed keratin preferably has a tensile strength higher than 15 MPa, more preferably higher than 16, 17, 18 or 20 MPa. The film preferably also has an E-modulus of at least 100 MPa, more preferably higher than 150, 200, 250 or 300 MPa. The film preferably also has an elongation at break of at least 10%, more preferably higher than 20, 30, 40 or 50%. A degree of hydrolysis of the solubilised keratin that allows to produce a keratin-based product with such physicochemical properties may be defined by means of the distribution of the molecular weights of the solubilised and partially hydrolysed keratin as obtained in the process of the invention. Thus, the distribution of the molecular weights of the solubilised and partially hydrolysed keratin may be defined as follows:

The solubilised and partially hydrolysed keratin essentially has a molecular weight of between 1 and 10.4 kDa, and in particular between 3 and 10.4 kDa, whereby essentially is understood to mean that at least 50%, preferably at least 90%, more preferably at least 95%, and most preferably at least 99% of all keratin molecules present in the partially hydrolysed keratin fraction have a molecular weight within the ranges indicated;

Preferably at least 1% of the solubilised keratin has a molecular weight less than 10 kDa In addition, preferably at least 50% of the solubilised keratin has a molecular weight of more than 5 kDa. More preferably, at least 3, 5, 7, 10 or 15% of the solubilised keratin has a molecular weight less than 10 kDa, whereby at least 60, 70, 80, 90 or 95% of the solubilised keratin has a molecular weight of more than 5 kDa; and/or The solubilised and partially hydrolysed the keratin preferably has molecular weight distribution that is essentially equal to a distribution of molecular weights of solubilised keratins that are obtained when 40 grams of cleaned and dried poultry feathers are solubilised in one liter of an aqueous solution of 0.05–0.5 M sodium sulphide at a pH between pH 10.0 and pH 13.5, at a temperature between 40 and 80° C. for 30–90 minutes. The solubilised keratins are then preferably separated from the undissolved starting material by filtration. More preferred, the molecular weight distribution is essentially equal to a distribution of molecular weights of keratin that is obtained when 40 grams of cleaned and dried poultry feathers are solubilised in one liter of an aqueous solution of 0.075–0.15 M sodium sulphide at a pH between pH 11.0 and pH 13.0, at a temperature between 55 and 65° C. for 45–75 minutes. Most preferred, the molecular weight distribution is essentially equal to a distribution of molecular weights of keratin that is obtained when 40 grams of cleaned and dried poultry feathers are solubilised in one liter of an aqueous solution of 0.1 M sodium sulphide at pH 12.5, at a temperature of 60° C. for 45–75 minutes.

The solubilised and partially hydrolysed keratin preferably has molecular weight distribution that is such that a 1% (w/v) solution of the solubilised keratin at 25° has a viscosity of between 1 mPa.s to 100 mPa.s, preferably between 1 mPa.s and 20 mPa.s. The viscosity may for instance be measured in an Ubbelohde viscosimeter.

The solubilised and partially hydrolysed the keratin preferably has molecular weight distribution that the solubilised keratin has a dispersibility in water of between 1% and 50%, preferably between 10% and 30%. The dispersibility of the keratin is herein defined in that the keratin is capable of forming a stable dispersion which shows little or no deposit within 24 hours after preparation.

The degree of hydrolysis may be controlled by suitably choosing the conditions of the hydrolysis reaction, including but not limited to the reactants used (e.g. for chemical degradation), the forces/equipment used (e.g. for physical degradation), the enzymes used (e.g. for enzymatic degradation), the time of hydrolysis, the temperature, the pH, the solvent(s) used, the concentrations of the respective reactants, the concentration of the keratin material, the manner in which the keratin material is provided (e.g. after suitable pre-treatment as described hereinbelow), any stirring or agitation used; and/or whether the hydrolysis is obtained during solubilisation, modification and/or separately. It is envisaged that the selection of the specific conditions that will provide the desired degree of hydrolysis—and that thereby, in conjunction with the partial modification and any further processing, lead to a final product with the desired properties, e.g. those described below—may require some preliminary experiments and/or some degree of trial and error. However, based upon the disclosure herein, this will be within easy reach of the skilled person and should therefore be considered encompassed within the scope of the invention.

In addition—or alternatively—the degree of hydrolysis may be determined in several ways, including e.g. analysis of the molecular weights of the hydrolysed fragments or the distribution thereof, e.g. by size exclusion chromatography; determination of the viscosity of the preparation; determination of dispersibility of the preparation; determination of the amount of protein end-groups; or any combination of these and other suitable techniques.

Depending upon the conditions used, a fraction or preparation of partially hydrolysed keratins with molecular weights that are essentially within the ranges indicated above may be obtained directly as a result of the partial hydrolysis. However, it is also within the scope of the invention that, in order to provide such a fraction or preparation, a certain amount of—and up to essentially all—higher molecular weight components still present (e.g. any remaining and undissolved starting material) and/or a certain amount of—and up to essentially all—lower molecular weight degradation products formed during the hydrolysis reaction, may be removed from the hydrolysed fraction or preparation, e.g. as part of any further processing after hydrolysis and/or modification.

Also, according to the invention, it is possible that the solubilised keratin may form aggregates, e.g. with molecular weights above the range(s) mentioned above. Such aggregation as well as the aggregates obtained are within the scope of the invention, as long as the keratin-derived molecules that form these aggregates have molecular weights that are essentially within the range(s) indicated.

Furthermore, it is also possible that some degree of polymerisation of the keratin-derived products takes place (e.g. after partial hydrolysis, partial modification and/or further processing), in which again products with molecular weights above the range(s) mentioned above may be formed. Such polymerisation as well as the polymeric products obtained are also within the scope of the invention, again provided that the keratin-derived molecules that combine to form these polymeric structures have molecular weights that are essentially within the range(s) mentioned above.

Compared to the essentially intact keratins of the prior art, the partially hydrolysed/modified keratins of the invention may advantageously be used in particularly those applications where keratins with a more hydrophobic character and/or a lower surface tension is required. This may be advantageous when the partially hydrolysed keratins of the invention are applied in films or coating. The partially hydrolysed keratins of the invention also have improved adhesive properties as compared to essentially intact keratins. These adhesive properties may e.g. be advantageously applied in sticking paper to glass as may be used in fixing labels onto (beer) bottles. Compared to the essentially intact keratins of the prior art, the partially hydrolysed keratins of the invention have improved emulgating properties as the partially hydrolysed keratins are more amphiphilic. A further benefit of using partially hydrolysed and partially modified keratins lies in the potentially increased antimicrobial effect of partially hydrolysed proteins. This was demonstrated for lactoferricin which is a hydrolysis product of the whey protein lactoferrin. By partial modification, the keratin peptide with increased antimicrobial effect can still be incorporated into a film with good mechanical strength by disulphide bond formation, leading to a new generation of anti-microbial coatings.

In a further optional aspect of the invention, the solubilised and partially modified keratin may be subjected to further processing steps, which may e.g. include:

further purification, e.g. to remove undesired components and/or substances from the keratin product obtained These may for instance include remaining keratin starting material, higher molecular weight keratin components, lower molecular weight keratin components, reactants and/or by-products from any of the processing steps, and/or other impurities or undesired components. Suitable techniques for removing such components or substances include e.g. washing, precipitation, dialysis, filtration and centrifugation;

isolation of the keratin-derived product, and/or of any specific part or fraction thereof. This may for instance be achieved using techniques such as precipitation, membrane separation, chromatographic techniques, and solvent extraction;

drying, including e.g. freeze-drying, spray-drying, multistage drying and drying using a roll;

dispersion in a desired solvent or mixture of solvents;

aggregation or even polymerisation;

or any suitable combination thereof.

Also, depending upon the intended use, the keratin product may be combined or mixed with one or more further substances, additives, components, etc. Some non limiting examples thereof include pigments, salts, anti-microbial agents, detergents, and plasticizers.

It will be clear that any such further processing and/or addition of after components may also be carried out by the end-user; and this is also encompassed within the scope of the invention.

A further aspect of the invention relates to compositions comprising the keratins obtained or obtainable by a process according to the invention as described above. The keratin in these compositions is characterised in that (a) its —SH groups are partially modified, preferably at least 10% and no more than 70% of the —SH groups of the keratin are modified; and (b) it is partially hydrolysed such that the keratins in the composition have a molecular weight distribution as specified herein above.

In another aspect, the invention discloses compositions comprising keratin, which compositions are obtainable (or obtained) in a process comprising at least the steps of (a) solubilising keratin from a keratin-fibre containing starting material in an aqueous solution of 0.05–0.5 M sodium sulphide at a pH between pH 10.0 and pH 13.5, at a temperature between 40 and 80° C. for 30–90 minutes; and (b) modifying between 10 and 70% of the —SH groups of the solubilised keratin, preferably by alkylation.

Generally, the product of the invention can be described as a keratinous (e.g. keratin-based or keratin-derived) product or a preparation or composition wherein partially hydrolysed and partially modified keratin molecules form the major component, e.g. for at least 50 wt. %, preferably at least 80, 90, 95 or 99 wt. %, of the total components in the product, preparation or composition. Preferably the partially hydrolysed and partially modified keratin molecules form at least 50 wt. %, preferably at least 80, 90, 95 or 99 wt. %, of the total protein in the product, preparation or composition. Thus, it is not excluded that the proteinaceous product of the invention may contain some other components, such as other proteins or protein constituents (e.g. hydrolysed and/or modified proteins), non-hydrolysed keratins, low(er) molecular weight hydrolysis products, as well as non-protein components such as surfactants, salts, and/or impurities such as dirt. However, these will only be present in minor amounts, e.g. of less than 50 wt. %, preferably less than 20 wt. %, more preferably less than 10 wt. %, even more preferably less than 5 wt. %.

Preferably at least 50, 60, 70, 80, or 90% of the keratin molecules in the compositions of the invention comprise at least one hydrophobic part or region and at least one, and preferably two hydrophilic parts or regions, as further described below. E.g., these keratin molecules may comprise a total of between 10 and 100 amino acid residues, preferably between 30 and 100 amino acid residues; in which the hydrophobic part or region comprises between 20 and 40 amino acid residues, the remaining amino acid residues constituting the hydrophilic part(s) or region(s). In a preferred aspect of the invention, the keratins in the composition are hydrolysed to such an extent that the resulting partially hydrolysed keratin molecules (still) contain at least a hydrophobic part or region—e.g. derived from the original central part ($\beta$) of the original keratin molecule—and at least one hydrophilic part or region, e.g. derived from one of the original chain ends (C) and/or (N). Such a partially hydrolysed keratin molecule can be considered to have the schematic structure "A-B" in which A represents the hydrophilic part or region, generally of between 5 to 30 amino acid residues; and B represents the hydrophobic part or region, generally of between 5 and 40 amino acid residues. Even more preferably, in the invention, the keratins are hydrolysed to such an extent that the resulting partially hydrolysed keratin molecules (still) contain at least a hydrophobic part or region—e.g. derived from the original central part ($\beta$) of the original keratin molecule—flanked on both ends by a hydrophilic part or region, e.g. one derived from the original chain end (C) and one derived from the original chain end (N). In this preferred aspect, the partially hydrolysed keratin molecule can be considered to have the schematic structure "A-B-A" in which both A's represents the hydrophilic parts or regions (e.g. as defined above) and B represents the hydrophobic part or region (also as defined above).

Because of this preferred structure A-B or even more preferred structure A-B-A, the partially hydrolysed keratins of the invention may be used with advantage to prepare or provide multi-phasic system—such as dispersions, emulsions, gels, micelles, microspheres—as well as layers or layered structures (including but not limited to single or double layers). Also, the partially hydrolysed keratins of the invention may be used as stabilisers, emulsifying agents or more generally formulating agents for such multi-phasic systems, which may be aqueous systems or organic systems. It will be clear to the skilled person that the water-soluble keratins or keratin-preparations described in the art, including but not limited to (more) fully hydrolysed preparations, will generally not be suited for such applications.

The compositions according to the invention will often be in the form of an aqueous solution or dispersion of the partially modified and partially hydrolysed keratins. Such solutions or dispersions will preferably contain at least 10, 20, or 40 g of keratins per liter and preferably no more than 60, 75, or 90 g of keratins per liter. Generally such solution or dispersions will contain about 50 g of keratins per liter. Preferably these solution or dispersion are stable in both a chemical and physical sense. Thus, in a chemical sense, no appreciable, i.e. preferably less than 10, 5, 1%, (further) degradation, modification and/or oxidation of the keratins occurs over a period of preferably at least a day, a week or a month. In a physical sense, no appreciable, i.e. preferably less than 10, 5, 1%, sedimentation or precipitation of the keratins occurs over a period of preferably at least a day, a week or a month. In order to stabilise the solutions or dispersions of the invention, additives known in the art per se may be applied. For longer-term storage or for more convenient transportation the compositions of the invention may be in a solid form, preferably in the form of a dispersible non-dusting powder or granulate. The usual techniques for drying and/or granulating may be applied, including the use of additives to aid in the formulation of the solid form.

A further aspect of the invention relates to a process for producing a keratin-based product using the partially modified and partially hydrolysed keratins of the invention as source of keratin. Preferred keratin-based products of the invention are produced by casting a solution or dispersion of the keratins of the invention.

Another aspect of the invention concerns the keratin-based product produced from the partially modified and partially hydrolysed keratins of the invention. In a preferred embodiment, the keratin-based product is a film or a coating casted from a solution or dispersion of the keratins of the inventions. Preferably, the film or a coating has a tensile strength higher than 15 MPa. The film or a coating preferably has an E-modulus higher than 100 MPa and preferably an elongation at break of more than 10%.

The partially modified and partially hydrolysed keratins of the invention may be used in any application for keratin-based products known in the art, including e.g. those applications mentioned in the prior art given hereinabove. Generally, in these applications, the keratin-derived products of the invention will provide favourable properties including but not limited to improved mechanical properties such as mechanical stability; improved physical and chemical stability; low solubility in water and good film-forming properties. In addition, because the keratin-derived product of the invention is water-dispersible instead of water-soluble, it may also be used in (the preparation of) for instance dispersions, emulsions, micelles, gels, microspheres or other multi-phasic aqueous systems. Thus, some non-limiting uses of the keratins of the invention include:

use as or in films, coatings, etc., or in the preparation thereof;
use as or in (biodegradable) packaging materials, or in the production thereof;
use as or in formulations such as controlled release systems, e.g. for active substances such as pharmaceuticals; agrochemicals such as herbicides, pesticides or other biocides; flavorings; perfumes; etc.;
use as or in the formation of emulsions, dispersions or other multi-phasic aqueous systems;
use as or in fillers, gelating agents, binders, bulking agents, granulating agents, release agents, matrix materials, emulsifiers, stabilisers or other formulating agents;
use as antioxidants;
use as anti-microbial agents.

As such, the keratins of the invention may for example find use in food products or in the field of food technology generally; in pharmaceutical and veterinary products; in cosmetics; in the field of agrochemicals; in adhesives; in paints or other coatings; in packaging materials; in cleansing agents such as detergents; in agriculture. Some specific uses of the keratins of the invention that are envisaged include, but are not limited to:

use as coating or binders for granules, powders etc. such as washing powder or other detergents;
use in general purpose adhesives, both for industrial as well as household use;
use in binder or adhesive for wood, paper, paperboard or moulded fibre;

use as binders in coatings—including but not limited to water-borne paint systems—and/or inks/ink systems; both for industrial as well as household use;

use as anti-oxidant;

use in encapsulating and/or coating technology;

use as anti-microbial agents in for instance animal feed and cosmetics.

EXAMPLES

Example 1

Figure 1A:
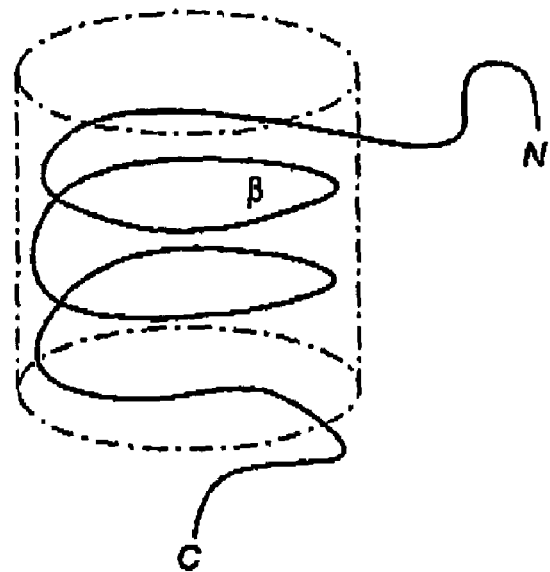
FIG. 1: Schematic representation of (A) a keratin molecule, (B) a microfibril consisting of polymerized keratin units and (C) the inter- and intra-molecular disulphide bonds in a microfibril.
Figure 1B:
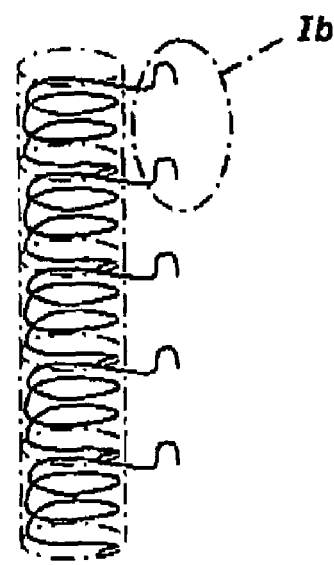
Figure 1C:
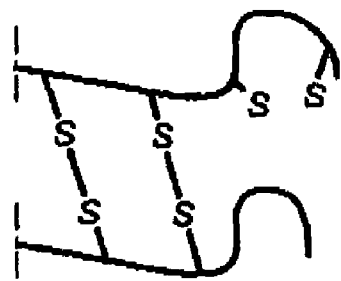

Preparation of Partially Modified Dispersible Keratins with and without Partial Degradation In one comparative experiment the procedure described by Schrooyen et al. (Journal of Agricultural and Food Chemistry; 2000; 48(9); 4326–4334) is used. Poultry feathers were cleaned using water and detergents. Cleaned and dried feathers (40 g) were mixed with one liter of an aqueous solution of 2-mercaptoethanol (125 mM), urea (8M) and EDTA (3 mM) in Tris-buffer (0.2 M, pH 9.0) and stirred for 1 hour. Undissolved feathers were separated from the dissolved keratins using a cheese cloth and a Whatman 54 filter (10 μm pore size). After filtration, 2 grams of monochloroacetic acid was added to the filtrate and the pH was kept constant at 9.0. After 1 hour the aqueous solution was dialysed and lyophilised. The yield of dry keratin product was 45%, based on 100% keratin starting material (weight of feathers). This product will be referred to as Modified Keratin—Method 1.

In a second experiment, a modified method, Method 2 was used. In comparison to Method 1, Method 2 differs in following aspects:
1) no urea is used
2) the pH is more alkaline (12.5 instead of 9.0)
3) a higher temperature is used (60° C. instead of 20° C.)

These conditions lead to partial degradation of the keratin proteins by hydrolysis. Cleaned and dried feathers (40 g) were mixed with one liter of a hot aqueous $Na_2S$-solution (0.1M, pH 12.5, 60° C.) and stirred for 1 hour. Undissolved feathers were separated from the dissolved keratins a cheese cloth and a Whatman 54 filter (10 μm pore size). After cooling to 20° C., 2 grams of monochloroacetic acid was added to the filtrate and the pH was set at 9.0 (yielding essentially 50% of SH-modification, referred to as 50%-Modified Keratin). After 1 hour the keratins were precipitated by setting the pH at 4.2 using hydrochloric acid (2N). The precipitates were isolated by centrifugation in a Sorvall centrifuge at 20,000×g for 30 minutes. A sample was taken from the supernatant and lyophilised for further analysis (further referred to as Modified Keratin Supenatant—Method 2). Keratin pellets were washed with acetic acid (0.1N, pH 4.2) and subsequently resuspended in water. The pH of the resuspended pellets was set at 7.0 using NaOH (1N) and these mixtures were freeze dried. The yield of dry keratin product was 40%, based on 100% keratin starting material (weight of feathers). This product will be referred to as Modified Keratin—Method 2.

Degree of Modification. The degree of modification was measured using DTNB/NTSB-assay as described by Schrooyen et al. (Journal of Agricultural and Food Chemistry; 2000; 48(9); 4326–4334). For Modified Keratin—Method 1, 54% of the cysteine residues were modified, for Modified Keratin—Method 2, 57% of the cysteine residues were modified.

Figure 2:
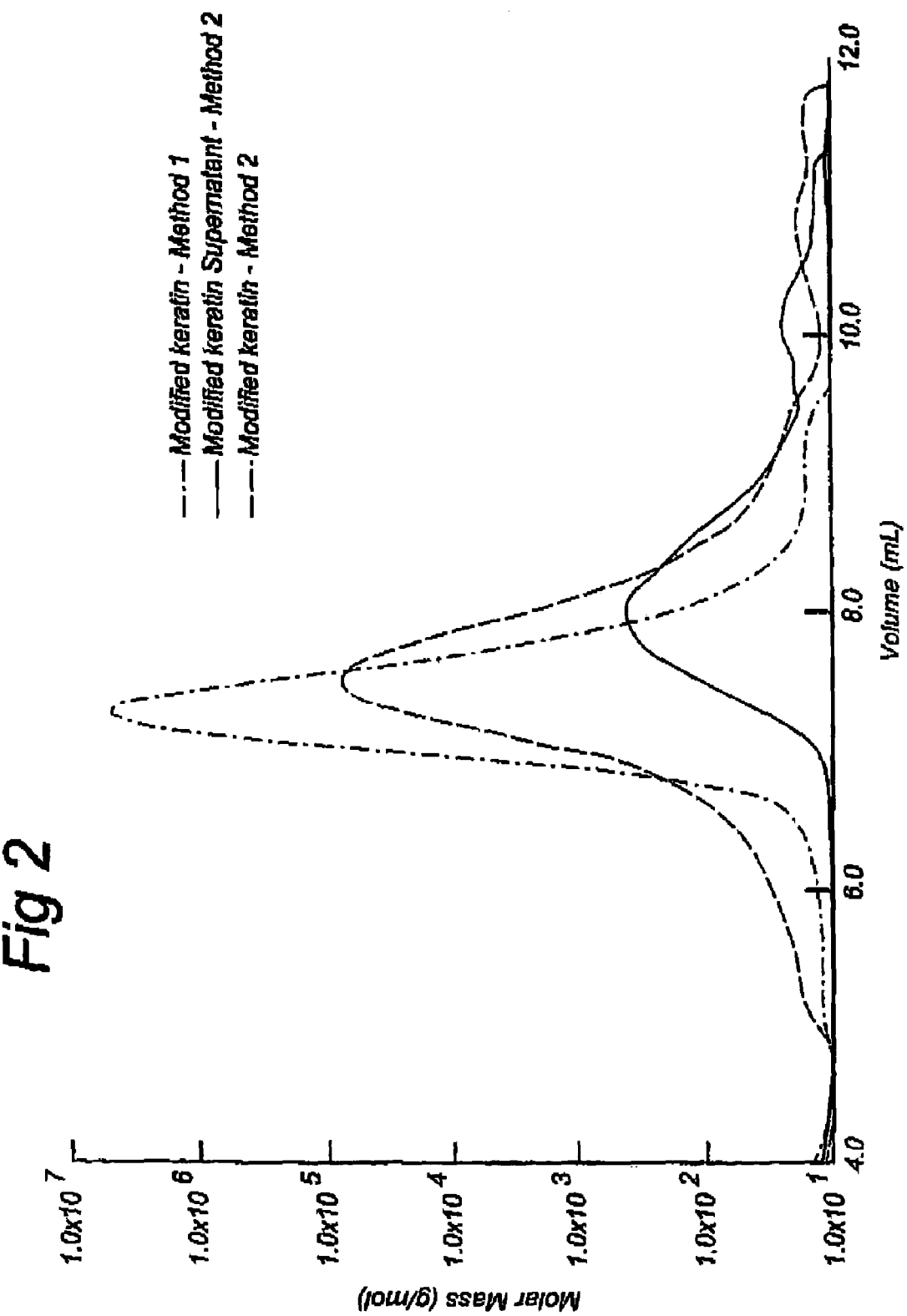
FIG. 2: A plot of the molar mass of three different modified keratin preparations versus the elution volume on a size exclusion column.

In FIG. 2, a plot of the molar mass versus the elation volume (TSK G 3000+TSK Guard PWH column+UV detector) is shown for Modified Keratin—Method 1, Modified Keratin Supernatant—Method 2 and Modified Keratin—Method 2. The eluent was an aqueous solution of urea (8M) and dithiothreitol (15 mM). The flow rate was 0.7 ml/min. Under these eluent conditions all remaining disulphide bonds are reduced and only the keratins (≈10,400 g/mol) or degradation products (less than 10,400 g/mol) are observed. It can be seen that both Modified Keratin—Method 1 and Modified Keratin—Method 2 have a similar molar mass distribution, although Modified Keratin—Method 2 contains more high and low molar mass products than Modified Keratin—Method 1. The high molar mass products are possibly products of cross-linking reactions which can occur at high pH, e.g. by lanthionine formation. Low molar mass products are the result of degradation. This can be observed even better in Modified Keratin Supernatant—Method 2, which still contains a large amount of low molar mass products, mainly between 3,000 and 10,000 g/mol.

As the pH used in Method 1 is never higher than 9.0, degradation of the polypeptide chain is unlikely to occur, as confirmed using SEC-MALLS analysis. In Method 2 the high temperature and strongly alkaline pH cause partial degradation of the keratins.

Example 2

Preparation of Partially Degraded Keratins with Various Degrees of Modification Poultry feathers were cleaned using water and detergents. Cleaned and dried feathers (60 g) were mixed with 1.5 liters of a hot aqueous $(NH_4)_2S$-solution (0.1M, pH 12.5, 60° C.) and stirred for 1 hour. Undissolved feathers were separated from the dissolved keratins using a cheese cloth and a Whatman 54 filter (10 μm pore size). The keratin yield in the filtrate was 59.5%, based on 100% keratin starting material (feathers). After cooling to 20° C., the filtrate was split in 3 parts of 500 ml each: to one part no monochloroacetic acid was added and the pH was set at 9.0 (yielding essentially unmodified keratin, referred to as Unmodified Keratin), to a second part 1 gram of monochloroacetic acid was added and the pH was set at 9.0 (yielding essentially 50% of SH-modification, refereed to as 50%-Modified Keratin), to a third part 5 grams of monochloroacetic acid was added and the pH was set at 9.0 (yielding essentially 90% of SH-modification, referred to as 90%-Modified Keratin). After 1 hour the keratins were precipitated by setting the pH at 4.2 using hydrochloric acid (2N). The precipitates were isolated by centrifugation in a Sorvall centrifuge at 20,000×g for 30 minutes. A sample was taken from the supernatant for analysis. Keratin pellets were washed with acetic acid (0.1N, pH 4.2) and subsequently resuspended in water. The pH of the resuspended pellets was set at 7.0 using NaOH (1N) and these mixtures were freeze dried. The yield of dry keratin product was 46.5% for Unmodified Keratin, 48.9% for 50%-Modified Keratin and 20.8% for 90%-Modified Keratin, based on 100% keratin starting material (weight of feathers).

Degree of Modification. The degree of modification was measured using DTNB/NTSB-assay as described by Schrooyen et al. (Journal of Agricultural and Food Chemistry; 2000; 48(9); 4326–4334), For Unmodified Keratin 1, 0% of the cysteine residues were modified, for 50% Modified Keratin 53% of the cysteine residues were modified, for 90%-Modified Keratin, 89% of the cysteine residues were modified.

Solubility

Figure 3:
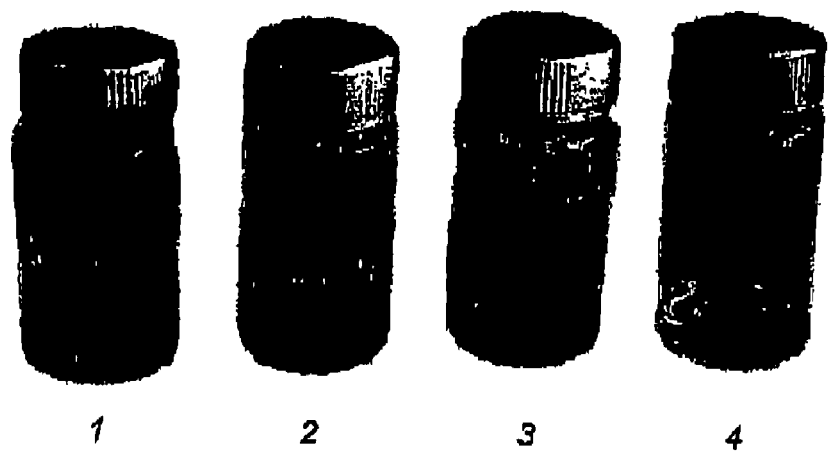
FIG. 3: Solubility of Unmodified Keratin in various solutions: (1) in water; (2) in 50 mM Tris-buffer pH 8.0, (3) in 8M urea at pH 8.5, and (4) in 8M urea at pH 8.5 supplemented with 2.5 g dithiothreitol (DTT) per liter.
Figure 4:
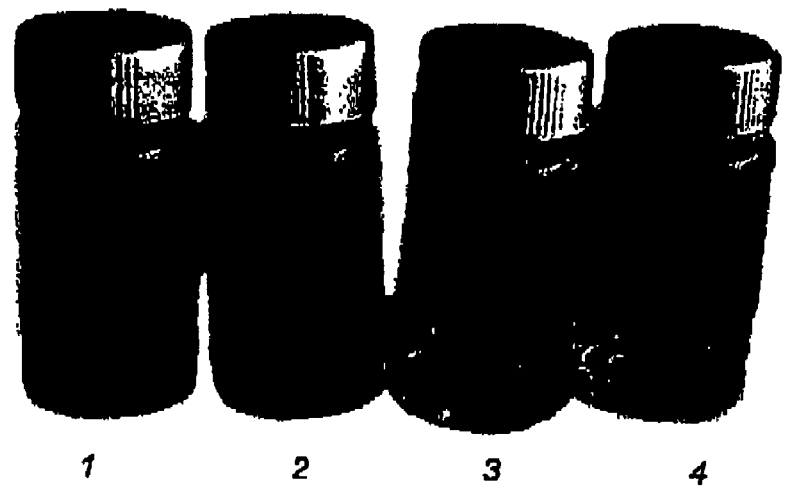
FIG. 4: Solubility of 50%-Modified Keratin in various solutions: (1) in water; (2) in 50 mM Tris-buffer pH 8.0, (3) in 8M urea at pH 8.5, and (4) in 8M urea at pH 8.5 supplemented with 2.5 g dithiotreitol (DTT) per liter.
Figure 5:
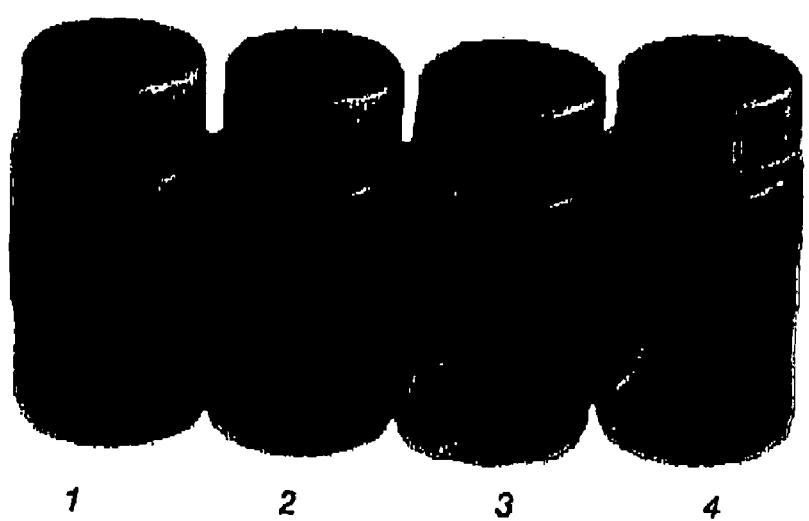
FIG. 5: Solubility of 90%-Modified Keratin in various solutions; (1) in water; (2) in 50 mM Tris-buffer pH 8.0, (3) in 8M urea at pH 8.5, and (4) in 8M urea at pH 8.5 supplemented with 2.5 g dithiothreitol (DTT) per liter.

The freeze dried keratin products were suspended (5%) in 4 buffers at room temperature:
1. Water
2. Aqueous Tris-buffer (50 mM)—pH 8.0: an alkaline pH helps to suspend keratins
3. Urea (8M)–pH 8.5: urea is added to prevent aggregation of non-covalently bound keratins
4. Urea (8M)+2.5 g, ltr Dithiothreitol (DTT)—pH 8.5: DTT is added to reduce disulphide bonds The Unmodified Keratin is completely soluble in Buffer 4 (FIG. 3). It forms a white gel in the other buffers. The 50%-Modified Keratin is soluble in Buffer 3 and 4 (FIG. 4). It forms a white gel in the other buffers. When buffer 2 is heated to 40° C. a turbid dispersion is obtained. The 90% -Modified Keratin is soluble or dispersible in all buffers; Buffer 1 and 2 remain somewhat turbid (FIG. 5).

Film Formation

To produce films by solution casting, a good dispersion or solution in water is necessary. From Unmodified Keratin it was not possible to produce films. From the 50%-Modified Keratin a 5%-dispersion was mixed with glycerol (0.30 g/g keratin) and cast in a petri dish. After drying, a strong film (tensile strength 15 MPa) was obtained, which was not soluble in water at room temperature. From the 90%-Modified Keratin a similar film was prepared. This film had bad mechanical properties (tensile strength<5 MPa) and was water soluble.

Adhesive Properties

The 50%-Modified Keratin had good adhesive properties and was especially suitable for sticking paper to glass, which is often used for beer bottles.

The invention claimed is:

1. A process for producing partially modified and partially hydrolysed keratin, the process comprises the steps of (a) solubilising keratin from a keratin-fibre containing starting material in an aqueous solution using a reducing agent at an alkaline pH of between pH 10 and pH 13.5 and at a temperature of at least 40° C., and (b) partially modifying the —SH groups of the solubilised keratin by alkylation, characterised in that the solubilised keratin is partially hydrolysed as a result of the conditions of steps (a) and (b) and an optional further hydrolysis step (c), whereby the solubilised keratin is partially hydrolysed such that at least 50% of the solubilised keratin molecules has a molecular weight higher than 1 kDa and less than 10.4 kDa and whereby the solubilised keratin has molecular weight distribution that is equal to a distribution of molecular weights of keratin that is obtained when 40 grams of cleaned and dried poultry feathers are solubilised in one liter of an aqueous solution of 0.05–0.5 M sodium sulphide at a pH between pH 10.0 and pH 13.5, at a temperature between 40 and 80° C. for 30–90 minutes.

2. The process according to claim 1, whereby the solubilised keratin is partially hydrolysed such that at least 1% of the solubilised keratin has a molecular weight less than 10 kDa, and at least 50% of the solubilised keratin has a molecular weight of more than 5 kDa.

3. The process according to claim 1, whereby at least 10% and no more than 70% of the —SH groups of the solubilised keratin are modified.

4. The process according to claim 1, whereby the reducing agent comprises a sulphide, preferably an alkali metal sulphide or ammoniumsulphide.

5. A composition comprising keratin, whereby the keratin is characterised in that: a) at least 10% and no more than 70% of the —SH groups of the keratin are modified by alkylation; and b) at least 50% solubilised keratin has a molecular weight of between 1 and 11 kDa and whereby the solubilised keratin has molecular weight distribution that is equal to a distribution of molecular weights of keratin that is obtained when 40 grams of cleaned and dried poultry feathers are solubilised in one liter of an aqueous solution of 0.05–0.5 M sodium sulphide at a pH between pH 10.0 and pH 13.5, at a temperature between 40 and 80° C. for 30–90 minutes.

6. The composition according to claim 5, whereby at least 1% of the keratin has a molecular weight less than 10 kDa, and at least 50% of the keratin has a molecular weight of more than 5 kDa.

7. A composition comprising keratin, whereby the composition is obtained in a process comprising the steps of: a) solubilising keratin from a keratin-fibre containing starting material in an aqueous solution of 0.05–0.5 M sodium sulphide at a pH between pH 10.0 and pH 13.5, at a temperature between 40 and 80° C. for 30–90 minutes; b) modifying between 10 and 70% of the —SH groups of the solubilised keratin by alkylation.

8. The composition according to claim 5, whereby the composition is in the form of an aqueous solution or dispersion.

9. The composition according to claim 5, whereby the composition is in a solid form, preferably in the form of a dispersible non-dusting powder or granulate.

10. A process for producing a keratin-based product, comprising adding a keratin containing composition as defined in claim 5 as a source of keratin.

11. The process according to claim 10, wherein the keratin-based product is produced by casting a solution or dispersion of said keratin containing composition.

12. The process of claim 11, wherein said process produces a keratin-based product that is a film or a coating.

13. A keratin-based product produced from a keratin containing composition as defined in claim 5, the product being a film or a coating with:
  a) a tensile strength of higher than 15 MPa;
  b) an E-modulus higher than 100 MPa; and
  c) an elongation at break higher than 10%.

14. A method for the preparation of a material selected from the group consisting of films or coatings; biodegradable packaging materials; formulations for controlled release systems for active substances; emulsions, dispersions or multiphasic aqueous systems; fillers, gelling agents, binders, bulking agents, granulating agents, release agents, matrix materials, emulsifiers, or stabilisers; an anti-oxidant;

and an anti-microbial agent comprising adding the keratin as defined in claim 5 to said material.

15. A biodegradable packaging material comprising the composition according to claim 5.

16. A formulation for controlled release of an active substance, comprising the composition according to claim 5.

17. An emulsion, dispersion or multiphasic aqueous system comprising the composition according to claim 5.

18. A filler, gelling agent, binder, bulking agent, granulating agent, release agent matrix material, emulsifier or stabilizer, comprising the composition according to claim 5.

19. An anti-oxidant comprising the composition according to claim 5.

20. An anti-microbial agent comprising the composition according to claim 5.

* * * * *